(12) United States Patent
Gerdts et al.

(10) Patent No.: US 9,393,141 B2
(45) Date of Patent: **\*Jul. 19, 2016**

(54) CATHETER

(71) Applicant: BOSTON SCIENTIFIC SCIMED, INC., Maple Grove, MN (US)

(72) Inventors: Michael D. Gerdts, Big Lake, MN (US); Karen Larson, Lino Lakes, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 129 days.

This patent is subject to a terminal disclaimer.

(21) Appl. No.: 14/223,620

(22) Filed: Mar. 24, 2014

(65) Prior Publication Data

US 2014/0194972 A1 Jul. 10, 2014

Related U.S. Application Data

(63) Continuation of application No. 12/820,782, filed on Jun. 22, 2010, now Pat. No. 8,685,076, which is a continuation of application No. 11/093,448, filed on Mar. 30, 2005, now Pat. No. 7,740,652.

(51) Int. Cl.
   - *A61F 2/06* (2013.01)
   - *A61F 2/966* (2013.01)
   - *A61F 2/95* (2013.01)

(52) U.S. Cl.
   CPC . *A61F 2/966* (2013.01); *A61F 2/95* (2013.01); *A61F 2002/9665* (2013.01)

(58) Field of Classification Search
   CPC .... A61F 2002/9665; A61F 2/95; A61F 2/966
   See application file for complete search history.

(56) References Cited

U.S. PATENT DOCUMENTS

| | | | |
|---|---|---|---|
| 5,026,377 A | 6/1991 | Burton | |
| 5,534,007 A | 7/1996 | St. Germain et al. | |
| 5,749,920 A * | 5/1998 | Quiachon | A61B 17/11 606/195 |
| 5,772,669 A | 6/1998 | Vrba | |
| 6,019,778 A | 2/2000 | Wilson | |
| 6,059,813 A | 5/2000 | Vrba et al. | |
| 6,117,140 A | 9/2000 | Munsinger | |
| 6,120,522 A | 9/2000 | Vrba et al. | |
| 6,123,723 A | 9/2000 | Konya et al. | |
| 6,139,524 A | 10/2000 | Killion | |
| 6,206,888 B1 | 3/2001 | Bicek et al. | |
| 6,391,050 B1 | 5/2002 | Broome | |
| 6,425,898 B1 | 7/2002 | Wilson et al. | |
| 6,602,226 B1 | 8/2003 | Smith et al. | |
| 6,626,934 B2 | 9/2003 | Blaeser | |
| 6,773,446 B1 | 8/2004 | Dwyer et al. | |
| 6,776,791 B1 | 8/2004 | Stallings | |
| 2001/0034548 A1 | 10/2001 | Vrba et al. | |
| 2004/0098083 A1 | 5/2004 | Tran et al. | |
| 2004/0267348 A1 | 12/2004 | Gunderson et al. | |
| 2005/0182475 A1 | 8/2005 | Jen et al. | |
| 2006/0074477 A1 | 4/2006 | Berthiaume et al. | |

FOREIGN PATENT DOCUMENTS

| | | |
|---|---|---|
| WO | 9717899 | 5/1997 |
| WO | 0018330 | 4/2000 |
| WO | 0023139 | 4/2000 |
| WO | 0027309 | 5/2000 |
| WO | 0071059 | 11/2000 |
| WO | 2004098692 | 11/2004 |
| WO | 2005020856 | 3/2005 |

\* cited by examiner

*Primary Examiner* — Gregory Anderson
(74) *Attorney, Agent, or Firm* — Seager, Tufte & Wickhem, LLP

(57) ABSTRACT

Catheters, as well as related systems and methods are disclosed.

20 Claims, 6 Drawing Sheets

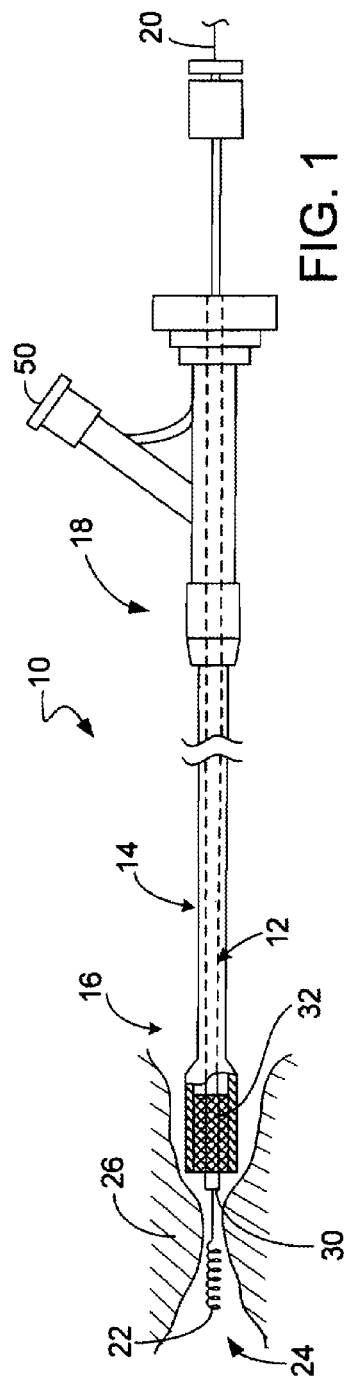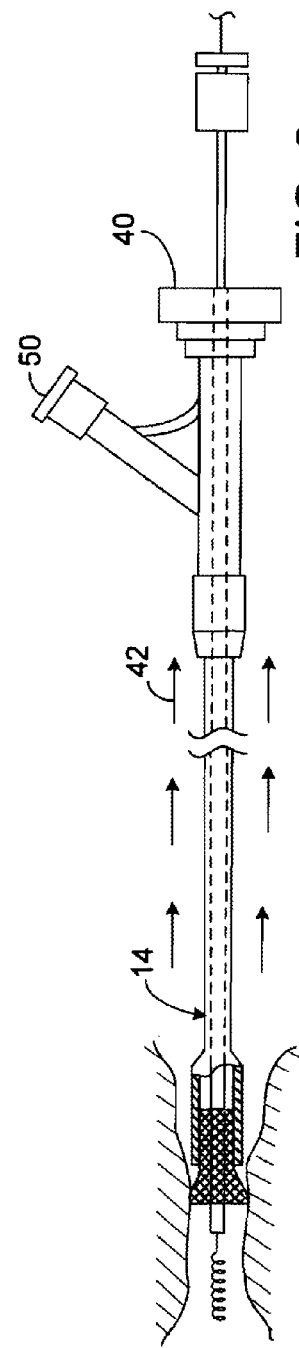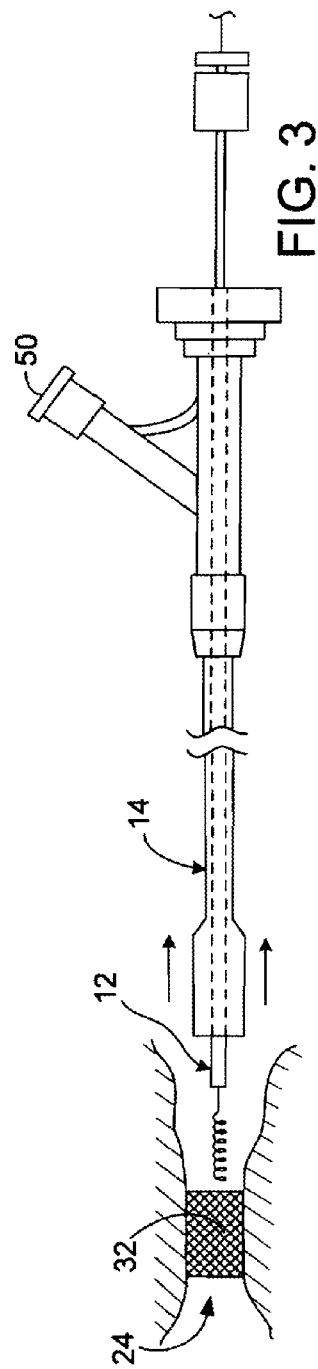

CATHETER

CROSS-REFERENCE TO RELATED APPLICATION

This application is a continuation of U.S. patent application Ser. No. 12/820,782, filed Jun. 22, 2010, which is a continuation of U.S. patent application Ser. No. 11/093,448, filed Mar. 30, 2005, now U.S. Pat. No. 7,740,652, the entire disclosures of which are hereby incorporated by reference.

TECHNICAL FIELD

This invention relates to systems for delivering medical devices, as well as related systems and methods.

BACKGROUND

Systems are known for delivering medical devices, such as stents, into a body lumen. Often, such systems include a proximal portion that remains outside the body during use and a distal portion that is disposed within the body during use. The proximal portion typically includes a handle that is held by an operator of the system (e.g., a physician) during use, and the distal portion can include a sheath surrounding a catheter with a stent positioned therebetween. Generally, the operator of the system positions the distal portion within the lumen at a desired location (e.g., so that the stent is adjacent an occlusion). The operator can then retract the sheath to allow the stent to engage the occlusion/lumen wall. Thereafter, the operator removes the distal portion of the system from the lumen.

SUMMARY

In general, the invention relates to systems for delivering medical devices, as well as related systems and methods. The systems can be used as, for example, implantable medical endoprosthesis delivery systems (e.g., stent delivery systems). The systems can be used, for example, to deploy a medical endoprosthesis (e.g., a stent) at a desired location within a lumen of a subject (e.g., an artery of a human).

In some embodiments, the systems include a catheter and a bumper disposed about the catheter. The catheter and bumper can be configured so that an implantable medical endoprosthesis can be disposed about the catheter distal to the bumper. The bumper can be configured to limit proximal movement of the endoprosthesis during deployment of the medical endoprosthesis.

In some embodiments, the system includes an outer sheath, which at least partially surrounds the catheter and bumper. An inner diameter defined by a portion of the sheath, e.g., by the proximal portion, may be smaller than a maximum outer diameter defined by the bumper.

The bumper may have at least some freedom of movement with respect to the catheter. For example, the bumper and catheter can be configured to allow the bumper to move longitudinally with respect to at least a distal portion of the catheter. The freedom of movement of the bumper with respect to the catheter can facilitate assembly of the system. For example, during assembly, the bumper can be introduced into the sheath through one end of the sheath, e.g., through a distal end of the sheath, and the catheter can be introduced into the sheath through the other end of the sheath, e.g., through a proximal end of the sheath.

Other features and advantages of the invention will be apparent from the description, drawings and claims.

DESCRIPTION OF DRAWINGS

FIGS. 1-3 are side views of an embodiment of an endoprosthesis delivery system during use.

FIG. 7b is a side view of an embodiment of a bumper for use with the inner catheter of FIG. 7a.

FIG. 7c is a side view of the bumper of FIG. 7b engaged with the inner catheter of FIG. 7a.

Like reference symbols in the various drawings indicate like elements.

DETAILED DESCRIPTION

Figure 4:
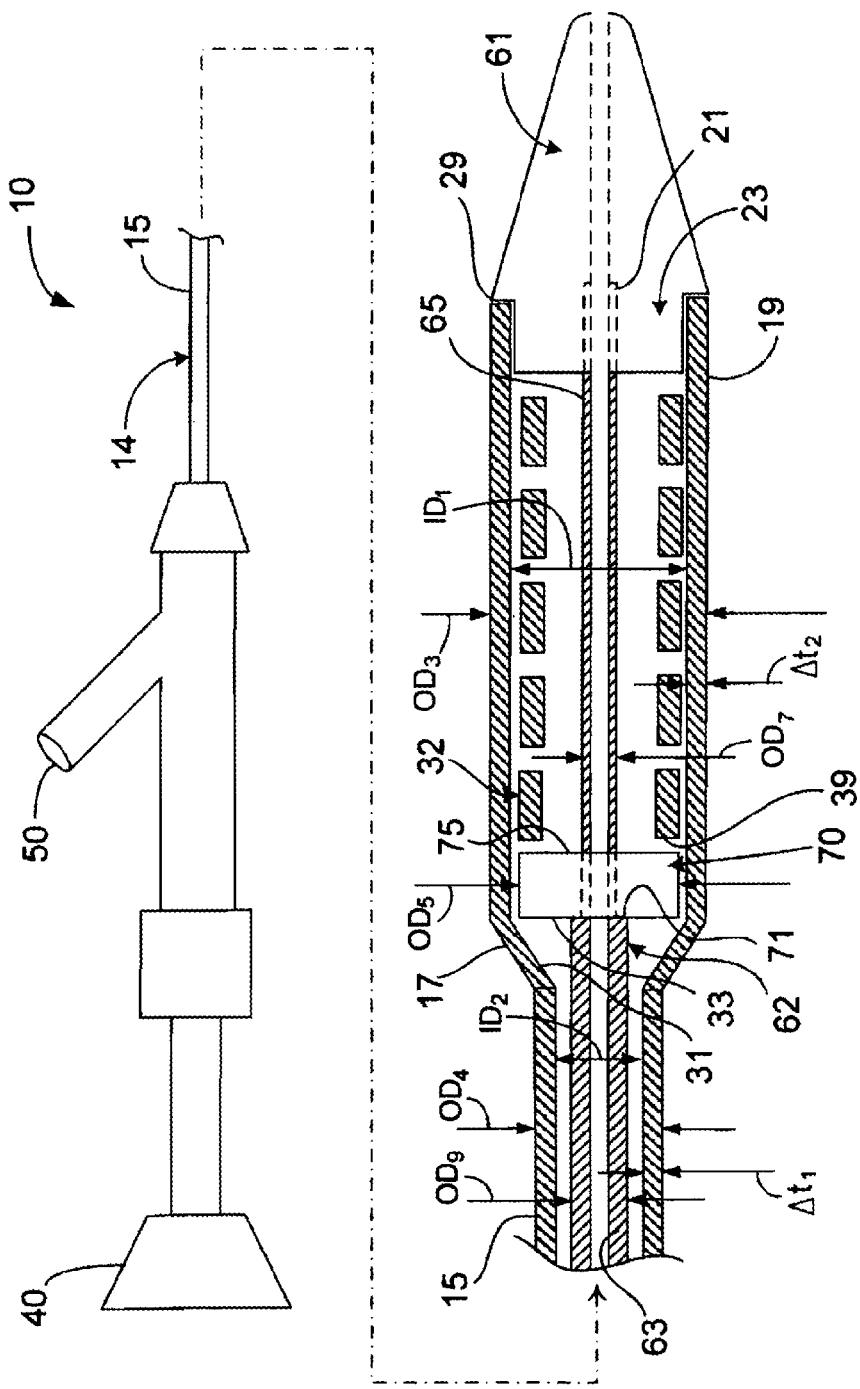
FIG. 4. is an exploded, mixed view of an embodiment of an endoprosthesis delivery system.

FIGS. 1-3 show an implantable medical endoprosthesis delivery system 10 that includes a catheter 12, a sheath 14 surrounding catheter 12, and a stent 32 positioned between catheter 12 and sheath 14. The delivery system 10 includes a distal end 16 dimensioned for insertion into a body lumen (e.g., an artery of a human) and a proximal end 18 that resides outside the body of a subject, and that contains at least one port 50 and lumens for manipulation by a physician. In an exemplary use of system 10, a guide wire 20 with a blunted end 22 is inserted into a body lumen 24 by making an incision in the femoral artery, and directing guide wire 20 to a constricted site 26 of lumen 24 (e.g., an artery constricted with plaque) using, for example, fluoroscopy as a position aid. After guide wire 20 has reached constricted site 26 of body lumen 24, catheter 12, stent 32 and sheath 14 are placed over the proximal end of guide wire 20. Catheter 12, stent 32 and sheath 14 are moved distally over guide wire 20 and positioned within lumen 24 so that stent 32 is adjacent constricted site 26 of lumen 24. Sheath 14 is moved proximally, allowing stent 32 to expand and engage constricted site 26. Sheath 14, catheter 12 and guide wire 20 are removed from body lumen 24, leaving stent 32 engaged with constricted site 26.

Referring also to FIG. 4, sheath 14 includes a proximal sheath portion 15 joined by a transition sheath portion 17 to a distal sheath portion 19, which has a distal end 29. Catheter 12 includes a tube 62 having a proximal tube portion 63 and a distal tube portion 65, which has a distal end 21. Stent 32 is housed between the distal sheath portion 19 and the distal tube portion 65. A distal tip 61 is secured about distal end 21 of distal tube portion 65 to assist navigation of the delivery system through body lumen 24.

Figure 5A:
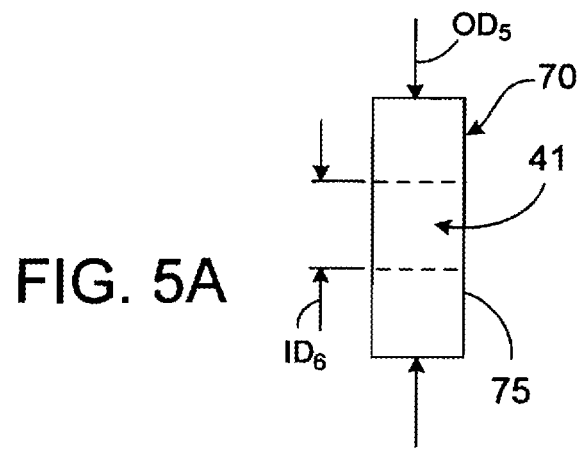
FIG. 5a is a side view of a bumper of the endoprosthesis delivery system of FIG. 4.
Figure 5B:
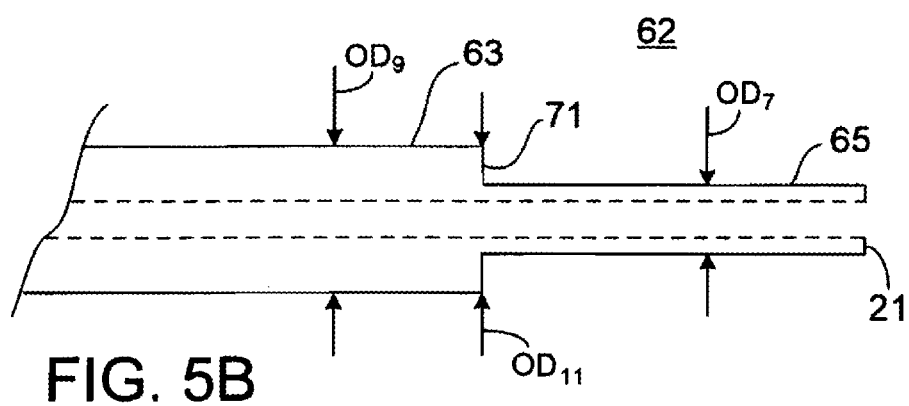
FIG. 5b is a partial side view of an inner catheter of the endoprosthesis delivery system of FIG. 4.

A bumper 70 is disposed about tube 62 proximal to stent 32. Referring also to FIG. 5a, bumper 70 has a distal face 75 that can engage a proximal portion 39 of stent 32. Referring also to FIG. 5b, tube 62 includes a unitary shoulder 71 formed by a portion of tube 62 having an outer diameter OD11 greater than a minimum inner diameter ID6 of a lumen 41 extending through bumper 70. Shoulder 71 and bumper 70 cooperate to ensure proper deployment of stent 32. For example, during withdrawal of sheath 14, friction between sheath 14 and stent 32 can urge the endoprosthesis proximally against bumper 70. The endoprosthesis can urge a proximal face 77 of bumper 70 against shoulder 71, which acts as a bumper stop to limit proximal motion of bumper 70. Hence, during withdrawal of sheath 14, bumper 70 can limit or prevent proximal movement of stent 32.

In addition to shoulder 71, other portions of tube 62 can limit proximal movement of bumper 70. For example, an outer diameter OD9 of proximal tube portion 63, e.g., adjacent and proximal to shoulder 71, is larger than minimum ID6 of bumper 70. Hence, in some embodiments, the outer diameter of proximal tube portion 63 can limit or prevent the bumper 70 from moving longitudinally along proximal tube portion. In some embodiments, the length of the proximal tube portion having an outer diameter larger than the inner diameter of the bumper extends for at least about 10%, e.g., at least about 25%, at least about 75%, of a length of the tube 62. As shown in FIG. 5b, the $OD_9$ of proximal tube portion 63 and ODn of shoulder 71 are the same. However, OD9 may be smaller or larger than ODn.

Figure 5C:
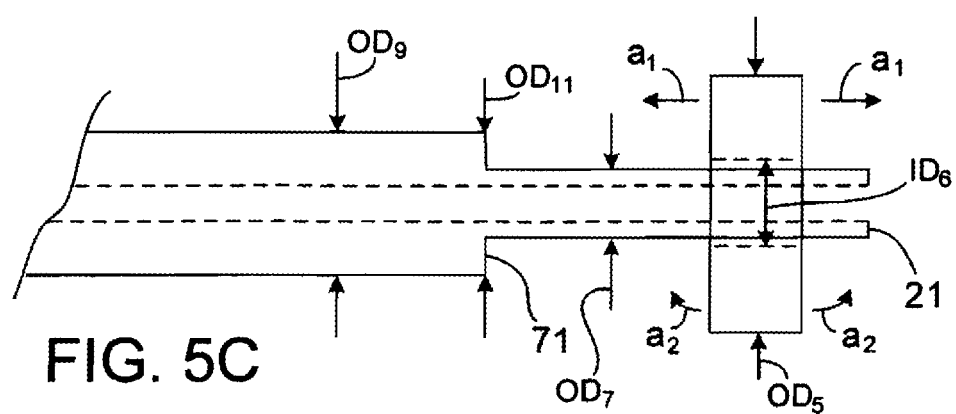
FIG. 5c is a partial side view of the inner catheter and bumper of FIGS. 5a and 5b illustrating freedom of movement between the inner catheter and bumper.

While shoulder 71 limits proximal movement of bumper 70 along tube 62, bumper 70 and distal tube portion 65 can be configured to allow at least some freedom of movement therebetween. As seen in FIG. 5c, ID6 of bumper 70 is larger than an outer diameter OD7 of distal tube portion 65. In some embodiments, bumper 70 has longitudinal freedom of movement, e.g., free sliding movement as indicated by arrows a1, along at least a portion of distal tube portion 65. The longitudinal freedom of movement allows bumper 70 to be passed over distal end 21 (when tip 61 is not secured over distal end 21) and moved along distal tube portion 65. When tip 61 is secured about distal end 21, the tip limits distal movement of bumper 70, e.g., tip 61 can prevent bumper 70 from sliding off distal tube portion 65. In some embodiments, bumper 70 can be moved freely, e.g., back and forth, along distal tube portion 65 between shoulder 71 of tube 62 and tip 61. As discussed below, longitudinal freedom of movement between bumper 70 and distal tube portion 65 can assist assembly of system 10.

In some embodiments, the freedom of movement includes tilting freedom of movement of bumper 70 with respect to distal tube portion 65 as indicated by arrows a2 of FIG. 5c. Such tilting movement allows the bumper to assume an orientation which most effectively, e.g., uniformly, engages stent 32. Bumper 70 may also or alternatively be provided with rotational freedom of movement with respect to distal tube portion 65. Without wishing to be bound by theory, it is believed that rotational freedom of movement enhances the ability of the bumper to uniformly engage stent 32.

As seen in FIG. 4, OD5 of bumper 70 is larger than ID2 of proximal sheath portion 15. In some embodiments, $OD_S$ is at least about 2%, e.g., at least about 3%, at least about 5%, at least about 10%, larger than ED2. In some embodiments, the length of the proximal sheath portion having an inner diameter less than the outer diameter of the bumper extends for at least about 10%, e.g., at least about 25%, at least about 75%, of a length of the sheath 14. In some embodiments, bumper 70 cannot move freely within proximal sheath portion 15 along its length without, for example, damage to either or both the bumper and proximal sheath portion.

In addition to freedom of movement between bumper 70 and distal tube portion 65, system 10 is configured to allow at least some freedom of movement between bumper 70 and sheath 14. For example, an outer diameter OD5 of bumper 70 is smaller than an inner diameter DD1 of distal sheath portion 19. Hence, bumper 70 can move freely within some or all of distal sheath portion 19.

In general, as seen in FIG. 4, an outer diameter OD3 of distal sheath portion 19 is larger than an outer diameter OD4 of proximal sheath portion 15. In some embodiments, ED2 of proximal sheath portion 15 is between about 0.044" and about 0.065", e.g., about 0.06"; ID1 of distal sheath portion 19 is between about 0.052" and 0.075", e.g., about 0.07"; OD7 of distal tube portion 65 is between about 0.032" and about 0.05", e.g., about 0.046"; OD5 of bumper 70 is between about 0.048" and about 0.07", e.g., about 0.065"; and DD6 of bumper 70 is between about 0.036" and 0.055".

A wall thickness At1 of proximal sheath portion 15 is larger than a wall thickness At2 of distal sheath portion 19. The larger wall thickness of proximal sheath portion 15 can reduce friction between proximal sheath portion 15 and proximal tube portion 63 as system 10 is introduced through a body lumen. For example, the larger proximal wall thickness can provide a yield strength and/or resistance to radial compression sufficient to limit or prevent buckling, which could cause the proximal sheath portion 15 to contact the tube 62 during navigation around sharp bends. Alternatively, or in combination, sheath portion 15 can be formed of less compressible materials than distal sheath portion 19.

Freedom of movement between bumper 70 and both distal tube portion 65 and distal sheath portion 19 facilitates assembly of system 10. Assembly can include introducing bumper 70 to distal sheath portion 19 via a distal opening 23 of sheath 14. Stent 32 is loaded in a radially compressed state into the distal sheath portion 19 via distal opening 23. For example, the endoprosthesis can be radially compressed by a plurality of irises or knife blades, which open sequentially allowing introduction of the stent into the sheath.

Tube 62 is introduced into distal sheath portion 19 via proximal sheath portion 15 and extended from proximal to distal through proximal sheath portion 15, through bumper 70 if already present, and then through stent 32 if already present. Shoulder 71 engages bumper 70. Engagement between the shoulder 71 and bumper 70 can facilitate a desired orientation between bumper 70 and stent 32. For example, in some embodiments, engagement between shoulder 71 and bumper 70 preferentially orients the bumper so that distal bumper face 75 is generally perpendicular to the longitudinal axis of distal sheath portion 14. Once distal tube portion 65 has been fully introduced into distal sheath portion 19, distal end 21 of tube 62 is accessible from, e.g., may extend from, distal opening 23 of sheath 14. Distal tip 61 is secured, e.g., mechanically and/or adhesively, with respect to distal end 21.

The order of assembly of system 10 can be varied. For example, tube 62 can be introduced in any order relative to bumper 70 and stent 32. In some embodiments, tube 62 is introduced into the distal sheath portion 19 after introducing both bumper 70 and stent 32. Alternatively, tube 62 can be introduced into distal sheath portion 19 after introducing bumper 70 but prior to introducing stent 32.

During loading, the endoprosthesis may contact bumper 70 and may move the bumper proximally within sheath 14. If tube 62 with shoulder 71 is not yet present within sheath 14, proximal sheath portion 15 and/or transition sheath portion 17 can limit bumper 70 (and stent 32) from moving proximal of the transition sheath portion 17. Transition portion 17 may be configured to orient bumper 70 so that distal face 75 is perpendicular to a longitudinal axis of distal sheath portion 19. For example, an inner surface 31 of transition portion 17 may be complementary to a proximal surface 33 of bumper 70. As stent 32 urges bumper 70 proximally, contact between inner surface 31 and proximal surface 33 encourages the perpendicular orientation of bumper face 75. After loading stent 32, bumper 70 may be left with at least some longitudinal freedom of movement with respect to sheath 14, e.g., between transition portion 17 and stent 32. After securing tip 61, the longitudinal freedom of movement allows tube 62 and distal tip 61 to be withdrawn proximally until a distal end 29 of sheath 14 forms an at least partial seal with tip 61.

In some embodiments, bumper 70 is formed of a polymeric material, which may be relatively incompressible. Exemplary materials include VESTAMID® (e.g., Nylon 12), a polyether-block co-polyamide polymer (e.g., PEBAX®) or a thermoplastic polyurethane elastomer (e.g., Pellethane™). In certain embodiments, bumper 70 is made of a metal or an alloy, such as, for example, stainless steel, Nitinol and/or platinum. Tip 61 is typically formed of a relatively soft polymeric material. Bumper 70 can be radiopaque or can include one or more radiopaque markers.

In general, sheath 14 and catheter 12 are at least partially formed of a polymeric material. Examples of polymeric materials include polyether-block co-polyamide polymers (e.g., PEBAX®), copolyester elastomers (e.g., Arnitel® copolyester elastomers), thermoplastic polyester elastomers (e.g., Hytrel®), thermoplastic polyurethane elastomers (e.g., Pellethane™), polyoelefins (e.g., Marlex® polyethylene, Marlex® polypropylene), HDPEs, low-density polyethylenes (LDPEs), polyamides (e.g., Vestamid®), polyetherether ketones (e.g., PEEK™), and combinations of these materials. Sheath 14 or catheter 12 may include an additive (e.g., a fluoropolymer, a silicone, an ultrahigh molecular weight polyethylene, an oil, or blends thereof) to assist in the movement of sheath 14 with respect to catheter 12 and stent 32. Sheath 14 may be a composite including, e.g., a reinforcing member, such as a braid or coil. Although transition portion 17 has tapered outer and inner diameters, other geometries may be used or transition portion 17 may be omitted altogether.

In some embodiments, at least a portion of the sheath 14, e.g., the transition sheath portion 17 and/or at least some of the distal sheath portion 19, allows visual confirmation of the bumper 70 within the sheath. For example, a portion of sheath 14 may have a transparent or translucent wall through which the bumper can be visualized. The bumper 70 may have a bright color and/or a color that contrasts with that of the sheath 14 to assist visual confirmation.

Stent 32 is typically formed of a shape memory alloy. Examples of shape memory alloys include nitinol, silver-cadmium (Ag—Cd), gold-cadmium (Au—Cd), gold-copper-zinc (Au—Cu—Zn), copper-aluminum-nickel (Cu—Al—Ni), copper-gold-zinc (Cu—Au—Zn), copper-zinc/(Cu—Zn), copper-zinc-aluminum (Cu—Zn—Al), copper-zinc-tin (Cu—Zn—Sn), copper-zinc-xenon (Cu—Zn—Xe), iron beryllium (Fe3Be), iron platinum (Fe3Pt), indium-thallium (In—Tl), iron-manganese (Fe—Mn), nickel-titanium-vanadium (Ni—Ti—V), iron-nickel-titanium-cobalt (Fe—Ni—Ti—Co) and copper-tin (Cu—Sn). For yet additional shape memory alloys, see, for example, Schetsky, L. McDonald, "Shape Memory Alloys", Encyclopedia of Chemical Technology (3rd ed.), John Wiley & Sons, 1982, vol. 20. pp. 726-736.

In embodiments discussed above, lumen 41 of bumper 70 has a constant internal diameter, ID6. However, bumpers with other internal geometries may be used.

Figure 6A:
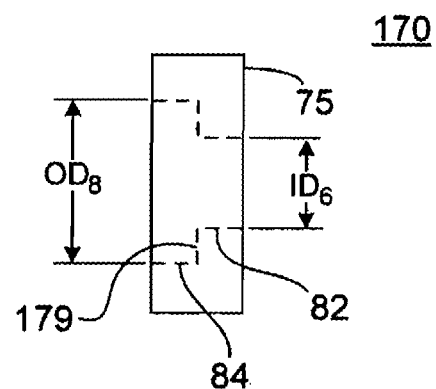
FIG. 6a is a side view of an embodiment of a bumper of an endoprosthesis delivery system.
Figure 6B:
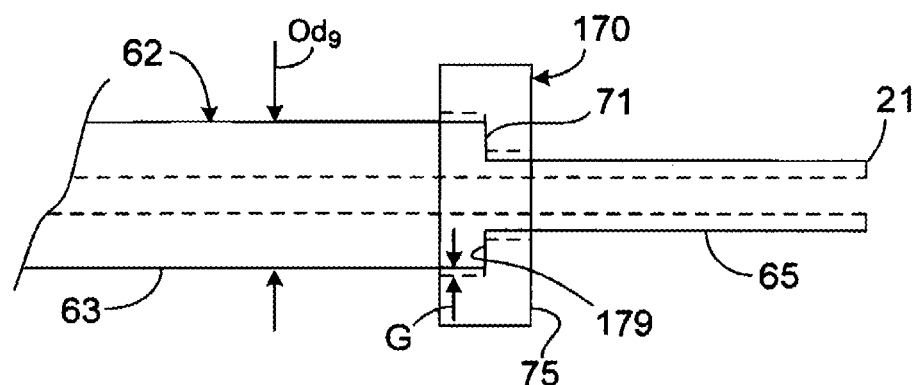
FIG. 6b is a side view of the bumper of FIG. 6a engaged with the inner catheter of FIG. 5b.

Referring to FIGS. 6a and 6b, a bumper 170 has a stepped inner diameter forming a bumper shoulder 179, which is generally complementary to shoulder 71 of tube 62. A first interior portion 82 of bumper 70 has inner diameter ID6 and a second interior portion 84 of bumper 170 has a larger inner diameter ID8, which is about as large as or larger than a OD11 of shoulder 71. Engagement between bumper shoulder 179 and tube 62 shoulder 71 limits bumper 170 from moving proximally of the shoulder. Bumper 170, however, has at least some freedom of movement, e.g., longitudinal, tilting, and/or rotational, with respect to distal tube portion 65.

In some embodiments, the engagement between a bumper and bumper stop, e.g., between shoulders 179, 71, establishes a mechanically secure fit requiring at least some level of force to disengage the bumper from the bumper stop. In other embodiments, the bumper can move freely in a distal direction even when engaged with a bumper stop. For example, a gap G exists between second interior portion 84 of bumper 170 and proximal tube portion 63 such that the engagement between shoulders 179, 71 prevents proximal movement of bumper 170 with respect to shoulder 171 but allows free distal movement of bumper 170 along distal tube portion 65. Gap G may be large enough to allow some tilting and/or rotational movement of bumper 170 relative to tube 62 even when shoulders 179, 71 are engaged.

The stepped inner diameter of bumper 170 can be fabricated by, e.g., injection molding. Alternatively, or in combination, the stepped inner diameter can be fabricated by machining the interior of the bumper after an initial fabrication step, e.g., an extrusion step.

Figure 7A:
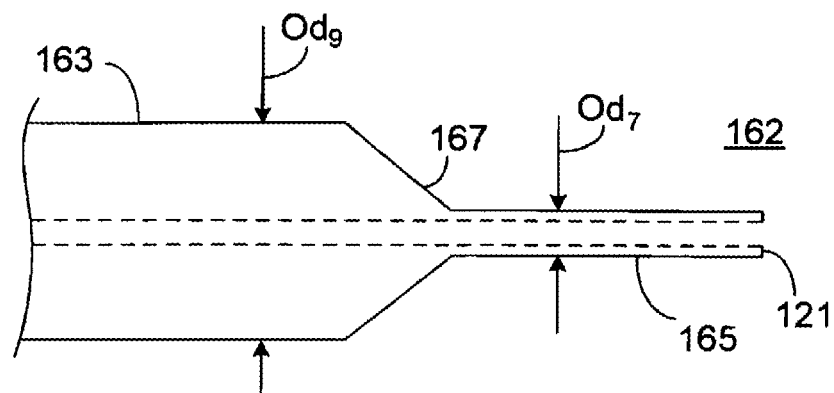
FIG. 7a is a partial side view of an embodiment of an inner catheter of an endoprosthesis delivery system.
Figure 7B:
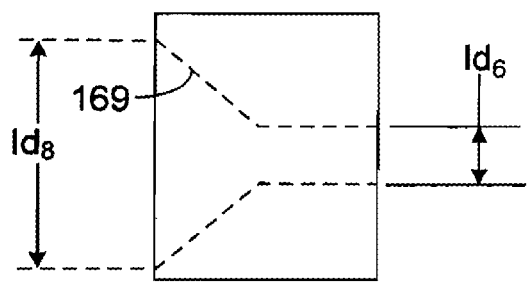
Figure 7C:
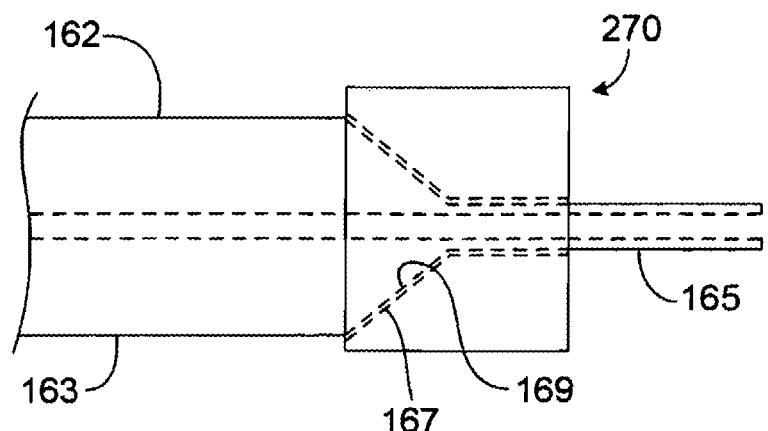

Referring to FIG. 7a, a tube 162 has a proximal tube portion 163 and a distal tube portion 165. A bumper stop, e.g., a sloped portion 167, gradually, e.g., uniformly, reduces the outer diameter of the tube 162 from the OD9 of proximal tube portion 163 to the smaller OD7 of distal tube portion 165. Referring also to FIG. 7b, a bumper 270 includes an interior surface 169 generally complementary to the sloped portion 167. The interior surface 169 transitions the inner diameter of the bumper 270 from the minimum ID6 to the larger ID8. Engagement between sloped portion 167 and surface 169 limits bumper 270 from moving proximally along proximal tube portion 63. As discussed for other bumpers herein, bumper 270, has at least some freedom of movement with respect to distal tube portion 165. Engagement between sloped portion 167 and surface 169 may be mechanically secure requiring force to move bumper 270 distally. Alternatively, the engagement may allow free distal movement of bumper 270.

Figure 8:
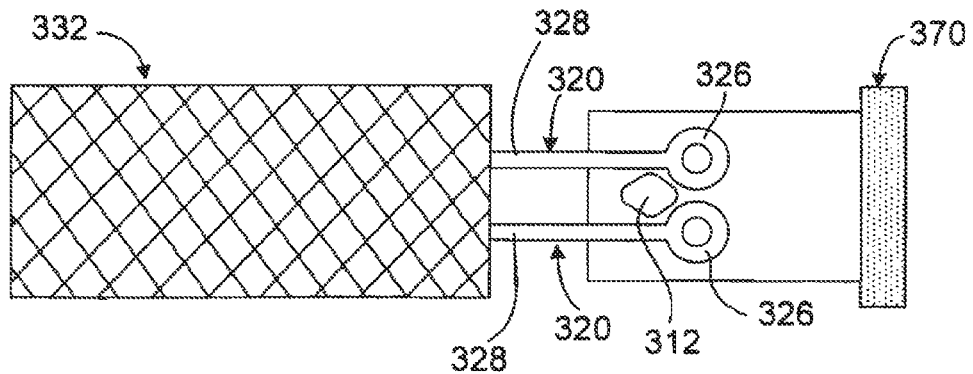
FIG. 8 is a side view of an embodiment of a bumper engaged with an endoprosthesis.

While bumpers described above include a distal face, which engages a stent to limit proximal stent motion, other forms of engagement between a bumper and stent are possible. For example, FIG. 8 shows a bumper 370, which has freedom of movement between a catheter and engages a stent 332 via interdigitation between paddles 320 of stent 332 and a bumper retainer 312 of bumper 370. Paddles 320 each include a head 326 and a leg 328 and may be formed of a flexible material. When paddles 320, which are pushed against bumper retainer 312, the paddles flex to extend heads 326 around the bumper retainer. Once heads 326 are pushed past bumper retainer 312, the heads return to their original configuration, thereby interdigitating paddles 320 about retainer 312. The interdigitation limits or prevents premature deployment of stent 332. On the other hand, paddles 320 can disengage retainer 312 when stent 332 radially expands at a desired deployment site.

Figure 9:
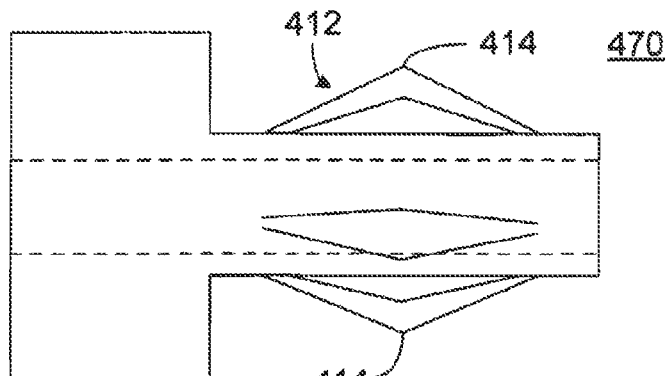
FIG. 9 is a side view of an embodiment of a bumper.

While bumper 370 interdigitates with paddles 320 projecting from stent 332, FIG. 9 shows a bumper 470 including a bumper retainer 412 with multiple peaks 414, which can engage an endoprosthesis from its interior. During loading, a portion of the endoprosthesis is slid over bumper 470. Bumper retainer 412 can be formed of a relatively soft polymer, such as a low durometer polyether-block co-polyamide polymer (e.g., a low durometer Pebax®), a thermoplastic resin (e.g., C-Flex®, a thermoplastic polyurethane (e.g., an aromatic polyether-based thermoplastic polyurethane such as Techothane®)), an elastomer, or silicone. Bumper retainer 470 can adjust to accommodate the endoprosthesis so that peaks 414 can interdigitate with the endoprosthesis, e.g., respective cells thereof. Bumper 470, like other bumpers described herein, has at least some freedom with respect to an inner catheter of a delivery system. Bumpers configured to engage an endoprosthesis by interdigitation are disclosed in U.S. application Ser. No. 10/822,251, filed Apr. 9, 2004, and incorporated herein by reference.

Figure 10:
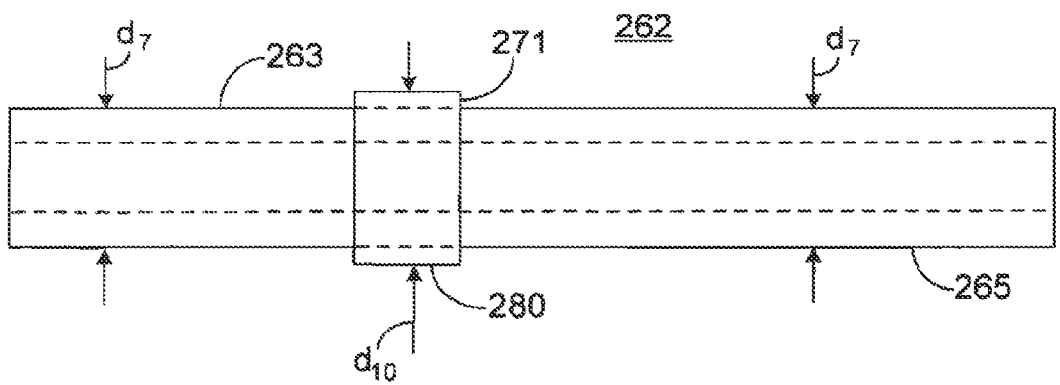
FIG. 10 is a partial side view of an embodiment of an inner catheter of an endoprosthesis delivery system.

While bumper stops unitary with a catheter have been described, other configurations can be used. For example, referring to FIG. 10, a tube 262 has a proximal tube portion 263 and a distal tube portion 265. A collar 280 having an outer diameter OD10 larger than OD7 of distal tube portion 265 surrounds tube 262 and forms a shoulder 271, which may operate as a bumper stop to engage a bumper as described for shoulder 71 of tube 62. Collar 280 may be secured to tube 262 mechanically, as by swaging, adhesively, or by a thermal process, e.g. heat shrinking.

Collar 280 is generally formed of a relatively incompressible material, e.g., a polymer or metal. Collar 280 may be radiopaque. In the embodiment shown, proximal and distal tube portions 263, 265 each have the same OD7. In other embodiments, tube 262 has different diameters along its length.

While certain embodiments have been described, other embodiments are possible.

As an example, while systems including a self-expanding stent have been described, other types of implantable medical endoprostheses can be used in the systems. For example, the implantable medical endoprosthesis can be a balloon-expandable implantable medical endoprostheses (e.g., a balloon-expandable stent). In such systems, inner catheter 12 would typically include an expandable balloon in the region around which the implantable medical endoprostheses is housed during delivery. Additional examples of implantable medical endoprostheses include stent-grafts and filters (e.g., arterial filters, venus filters).

What is claimed is:

1. A medical device, comprising:
    an inner tubular member having a proximal end, a distal end and a shoulder, wherein the tubular member has a first outer diameter between the proximal end and the shoulder; and a second outer diameter between the shoulder and the distal end, wherein the second outer diameter is smaller than the first outer diameter;
    a floating bumper disposed along the second region of the inner tubular member, the floating bumper having an inner diameter that is smaller than the first outer diameter and that is larger than the second outer diameter;
    an expandable implant disposed along the inner tubular member and disposed distally of the floating bumper; and
    a sheath disposed over the inner tubular member.

2. The medical device of claim 1, wherein the floating bumper is capable of translating along the first region.

3. The medical device of claim 1, wherein the floating bumper is capable of tilting relative to the inner tubular member.

4. The medical device of claim 1, wherein the floating bumper is capable of rotating relative to the inner tubular member.

5. The medical device of claim 1, wherein the inner diameter of the floating bumper is constant.

6. The medical device of claim 1, wherein the inner diameter of the floating bumper varies along the length thereof.

7. The medical device of claim 1, wherein a tip member is coupled to the first region of the inner tubular member.

8. The medical device of claim 7, wherein the tip member has a proximal shoulder and a proximal ledge extending proximally from the proximal shoulder.

9. The medical device of claim 8, wherein the sheath is capable of extending along the proximal ledge and abutting the proximal shoulder.

10. The medical device of claim 1, wherein the expandable implant includes a self-expanding stent.

11. The medical device of claim 1, wherein the sheath have a first section having a first inner diameter and a second section having a second inner diameter greater than the first inner diameter.

12. The medical device of claim 11, wherein the second section of the sheath is disposed adjacent to the second region of the inner tubular member.

13. A self-expanding stent delivery system, comprising:
    an inner tubular member having a first region with a first outer diameter and a second region distal of the first region with a second outer diameter that is smaller than the first outer diameter;
    a floating bumper disposed along the second region of the inner tubular member, the floating bumper having a first inner diameter and a second inner diameter, wherein the first inner diameter is larger than the second diameter, wherein the first inner diameter is larger than the first outer diameter and wherein the second inner diameter is smaller than the first outer diameter and that is larger than the second outer diameter;
    a self-expanding stent disposed along the inner tubular member and disposed distally of the floating bumper;
    a sheath disposed over the inner tubular member; and
    wherein the sheath is capable of shifting between a delivery configuration where the sheath extends over the self-expanding stent and a deployment configuration where the sheath is disposed proximally of the self-expanding stent.

14. The self-expanding stent delivery system of claim 13, wherein the floating bumper is capable of translating along the first region.

15. The self-expanding stent delivery system of claim 13, wherein the floating bumper is capable of tilting relative to the inner tubular member.

16. The self-expanding stent delivery system of claim 13, wherein the floating bumper is capable of rotating relative to the inner tubular member.

17. The self-expanding stent delivery system of claim 13, wherein a tip member is coupled to the first region of the inner tubular member.

18. The self-expanding stent delivery system of claim 17, wherein the tip member has a proximal shoulder and a proximal ledge extending proximally from the proximal shoulder, and wherein the sheath is capable of extending along the proximal ledge and a butting the proximal shoulder when the sheath is in the delivery configuration.

19. The self-expanding stent delivery system of claim 13, wherein the sheath have a first section having a first inner diameter and a second section having a second inner diameter greater than the first inner diameter, and wherein the second section of the sheath is disposed adjacent to the second region of the inner tubular member.

20. A self-expanding stent delivery system, comprising:
an inner tubular member having a proximal end, a distal end and a shoulder, wherein the tubular member has a first outer diameter between the proximal end and the shoulder; and a second outer diameter between the shoulder and the distal end, wherein the second outer diameter is smaller than the first outer diameter;
a floating bumper disposed along the second region of the inner tubular member, the floating bumper having a first inner diameter, a second inner diameter and a shoulder, wherein the first inner diameter is larger than the second diameter, wherein the first inner diameter is larger than the first outer diameter and wherein the second inner diameter is smaller than the first outer diameter and that is larger than the second outer diameter;
a self-expanding stent disposed along the inner tubular member and disposed distally of the floating bumper;
a deployment sheath slidably disposed along the inner tubular member;
wherein the shoulder of the inner tubular member is configured to mate with the shoulder of the floating bumper;
wherein the deployment sheath is capable of shifting between a delivery configuration where the deployment sheath extends over the self-expanding stent and a deployment configuration where the deployment sheath is disposed proximally of the self-expanding stent;
wherein the deployment sheath have a first section having a first inner diameter and a second section having a second inner diameter greater than the first inner diameter; and
wherein the second section of the deployment sheath is disposed adjacent to the second region of the inner tubular member.

* * * * *